United States Patent
Medasani et al.

(10) Patent No.: US 8,962,039 B2
(45) Date of Patent: Feb. 24, 2015

(54) METHOD OF TREATMENT OF NEURODEGENERATIVE OR NEURO-MUSCULAR DEGENERATIVE DISEASES AND THERAPEUTIC AGENT TO TREAT THE SAME

(75) Inventors: Munisekhar Medasani, Hyderabad (IN); Satyasayee Babu Divi, Vishakapatnam (IN); Satya Laxmi Priyanka Palempati, Hyderabad (IN)

(73) Assignee: Munisekhar Medasani, Hyderabad (IN)

( * ) Notice: Subject to any disclaimer, the term of this patent is extended or adjusted under 35 U.S.C. 154(b) by 0 days.

(21) Appl. No.: 13/391,516

(22) PCT Filed: Sep. 2, 2010

(86) PCT No.: PCT/IN2010/000583
§ 371 (c)(1),
(2), (4) Date: Feb. 21, 2012

(87) PCT Pub. No.: WO2011/027363
PCT Pub. Date: Mar. 10, 2011

(65) Prior Publication Data
US 2012/0164245 A1    Jun. 28, 2012

(30) Foreign Application Priority Data
Sep. 4, 2009  (IN) .......................... 2149/CHE/2009

(51) Int. Cl.
| | |
|---|---|
| *A61K 36/00* | (2006.01) |
| *A61K 31/34* | (2006.01) |
| *A61K 31/375* | (2006.01) |
| *A61K 9/00* | (2006.01) |
| *A61K 9/70* | (2006.01) |
| *A61K 31/315* | (2006.01) |
| *A61K 33/30* | (2006.01) |

(52) U.S. Cl.
CPC ............. *A61K 31/375* (2013.01); *A61K 9/0043* (2013.01); *A61K 9/0095* (2013.01); *A61K 9/7084* (2013.01); *A61K 31/315* (2013.01); *A61K 33/30* (2013.01)
USPC .......................................... 424/725; 514/474

(58) Field of Classification Search
None
See application file for complete search history.

(56) References Cited

U.S. PATENT DOCUMENTS

| | | | |
|---|---|---|---|
| 4,956,391 A * | 9/1990 | Sapse ............................. | 514/391 |
| 5,738,873 A | 4/1998 | Bleiweiss et al. | |
| 7,731,993 B2 * | 6/2010 | Berkson et al. ............... | 424/725 |
| 2004/0067993 A1 * | 4/2004 | Nakata et al. .................. | 514/370 |
| 2006/0149089 A1 | 7/2006 | Malfroy-Camine et al. | |
| 2007/0048296 A1 | 3/2007 | Kajander et al. | |
| 2009/0176715 A1 | 7/2009 | Javitt | |

FOREIGN PATENT DOCUMENTS

KR    2007061493 A * 6/2007

OTHER PUBLICATIONS

Aderinwale et al, Current therapies and new strategies for the management of Alzheimers disease. American Journal of Alzheimer's Disease and other Dementias, (Aug. 2010) vol. 25, No. 5, pp. 414-424.*
Ryan et al, Correlating familial Alzheimers disease gene mutations with clinical phenotype. Biomarkers in Medicine, (Feb. 2010) vol. 4, No. 1, pp. 99-112.*
Zhang, Loss of function of ATXN1 increases amyloid beta-protein levels by potentiating beta-secretase processing of beta-amyloid precursor protein. The Journal of biological chemistry, (Mar. 19, 2010) vol. 285, No. 12, pp. 8515-8526.*
Corvol teaches Neuroprevention: A new challenge? Revue Neurologique, (Nov. 2012) vol. 168, No. 11, pp. 796-801.*
Bacskai, Four-dimensional multiphoton imaging of brain entry, amyloid binding, and clearance of an amyloid-beta ligand in transgenic mice. Proceedings of the National Academy of Sciences of the United States of America, (Oct. 14, 2003) vol. 100, No. 21, pp. 12462-12467.*
Schenk, Immunotherapy with beta-amyloid for Alzheimer's disease: a new frontier. DNA and cell biology, (Nov. 2001) vol. 20, No. 11, pp. 679-681.*
Nechiporuk, Linkage of familial Alzheimer disease to chromosome 14 in two large early-onset pedigrees: effects of marker allele frequencies on lod scores. American journal of medical genetics, (May 1, 1993) vol. 48, No. 1, pp. 63-66.*
Davis, Comparative study of inhibition at multiple stages of amyloid-beta self-assembly provides mechanistic insight. Molecular pharmacology, (Aug. 2009) vol. 76, No. 2, pp. 405-413. Electronic Publication Date: May 29, 2009.*
Zager et al., "The Influence of Mannitol on Myoglobinuric Acute Renal Failure: Functional, Biochemical, and Morphological Assessments," *Journal of the American Society of Nephrology*, vol. 2, No. 4, pp. 848-855, 1991.
Lin et al., "The Early Response of Mannitol Infusion in Traumatic Brain Injury," *Acta Neurologica Taiwanica*, vol. 17, No. 1, pp. 26-32, Mar. 2008.

(Continued)

*Primary Examiner* — Qiuwen Mi
(74) *Attorney, Agent, or Firm* — Oliff PLC

(57) ABSTRACT

Use of high doses above 1 gm per day of ascorbic acid or the derivatives thereof for the treatment of neurodegenerative and neuro-muscular degenerative diseases and disorders, in particular amytrophic lateral sclerosis, multiple sclerosis, alzheimer's disease, parkinson's disease, and muscular dystrophy is disclosed. Preferably the dose includes mannitol which facilitates the delivery of ascorbic acid to the target cells in the brain. Still further the said dose includes zinc citrate for preventing formation of kidney stones. Dose compositions for various routes of application such as oral, intravenous, intramuscular, nasal and in the form of transdermal patches are discussed.

14 Claims, No Drawings

(56) References Cited

OTHER PUBLICATIONS

Sirivella et al., "Mannitol, furosemide, and dopamine infusion in postoperative renal failure complicating cardiac surgery," *The Annals of Thoracic Surgery*, vol. 69, pp. 501-506, 2000.

Kim et al., "Effect of Mannitol on Serum and Urine Electrolyte in Neurosurgical Patients," *The Journal of the Korean Society of Anesthesiologists*, vol. 25, No. 3, pp. 553-558, 1992 (with partial translation).

Luecke et al., "Zinc Deficiency in the Rat: Effect on serum in intestinal alkaline phosphatase activities," *The Journal of Nutrition*, vol. 94, No. 3973, pp. 344-350, 1968.

Lowry et al., "The Quantitative Histochemistry of Brain: II. Enzyme Measurements," *The Journal of Biological Chemistry*, vol. 207, No. 7, pp. 19-37, 1954.

Noseworthy et al., "Zinc Deficiency Exacerbates Loss in Blood-Brain Barrier Integrity Induced by Hyperoxia Measured by Dynamic MRI (44477)," *P.S.E.B.M.*, vol. 223, pp. 175-182, 2000.

Chvapil et al., "Effect of Zinc on Lipid Peroxidation and Metal Content in Some Tissues of Rats," *The Journal of Nutrition*, vol. 104, pp. 434-443, 1974.

Bray et al., "Effect of Dietary Zinc on Endogenous Free Radical Production in Rat Lung Microsomes," *The Journal of Nutrition*, vol. 116, pp. 1054-1060, 1986.

Hennig et al., "Antioxidant-Like Properties of Zinc in Activated Endothelial Cells," *Journal of the American College of Nutrition*, vol. 18, No. 2, pp. 152-158, 1999.

Liochev et al., "Copper- and Zinc-containing Superoxide Dismutase Can Act as a Superoxide Reductase and a Superoxide Oxidase," *The Journal of Biological Chemistry*, vol. 275, No. 49, pp. 38482-38485, Dec. 8, 2000.

Haramoto et al., "Essential Role of Ascorbic Acid in Neural Differentiation and Development: High Levels of Ascorbic Acid 2-Glucoside Effectively Enhance Nerve Growth Factor-Induced Neurite Formation and Elongation in PC12 Cells," *Journal of Health Science*, vol. 54, No. 1, pp. 43-49, 2008.

Frei, "Efficacy of Dietary Antioxidants to Prevent Oxidative Damage and Inhibit Chronic Disease," *The Journal of Nutrition*, vol. 134, pp. 3196S-3198S, 2004.

Singh et al., "Free Radicals and Oxidative Stress in Neurodegenerative Diseases: Relevance of Dietary Antioxidants," *Journal, Indian Academy of Clinical Medicine*, vol. 5, No. 3, pp. 218-225, 2004.

De Freitas et al., "Myenteric neurons and intestinal mucosa of diabetic rats after ascorbic acid supplementation," *World Journal of Gastroenterology*, vol. 14, No. 42, pp. 6518-6524, Nov. 14, 2008.

Nikam et al., "Oxidative Stress in Parkinson's Disease," *Indian Journal of Clinical Biochemistry*, vol. 24, No. 1, pp. 98-101, 2009.

Kontush et al., "Influence of Vitamin E and C Supplementation on Lipoprotein Oxidation in Patients With Alzheimer's Disease," *Free Radical Biology & Medicine*, vol. 31, No. 3, pp. 345-354, 2001.

Takanaga et al., "Sodium-dependent ascorbic acid transporter family SLC23," *European. Journal of Physiology.*, vol. 447, pp. 677-682, 2004.

Caprile et al., "The Na+-dependent L-ascorbic acid transporter SVCT2 expressed in brainstem cells, neurons, and neuroblastoma cells is inhibited by flavonoids," *Journal of Neurochemistry*, vol. 108, pp. 563-577, 2009.

Martin et al., "Roles of Vitamins E and C on Neurodegenerative Diseases and Cognitive Performance," *Nutrition Reviews*, vol. 60, No. 11, pp. 308-326, 2002.

Gilgun-Sherki et al., "Oxidative Stress Induced-Neurodegenerative Diseases: The Need for Antioxidants That Penetrate the Blood Brain Barrier," *Neuropharmacology*, vol. 40, pp. 959-975, 2001.

Apr. 29, 2011 International Search Report issued in International Application No. PCT/IN2010/000583.

\* cited by examiner

METHOD OF TREATMENT OF NEURODEGENERATIVE OR NEURO-MUSCULAR DEGENERATIVE DISEASES AND THERAPEUTIC AGENT TO TREAT THE SAME

This invention relates to a composition, and method for the prevention, elimination, treatment and management of neurodegenerative and neuro muscular-degenerative disorders and diseases in human and animal subjects.

Some of the neurodegenerative and neuro muscular-degenerative disorders and diseases in human and animal subjects to which the composition and method of the present invention are particularly applicable are:
1. Amytrophic Lateral Sclerosis (ALS),
2. Multiple Sclerosis (MS),
3. Alzheimer's disease (AD),
4. Parkinson's disease (PD), and
5. Muscular Dystrophy (MD).

These inventors observe that the applicability of the composition and method of the invention extends to all said disorders and diseases and particularly to the five mentioned hereinabove. While the composition and the method of the invention has wide applicability over the whole range of said neurodegenerative and neuro muscular-degenerative disorders and diseases, the further description hereinbelow is constructed on the basis of the applicability thereof to only said five disorders and diseases. This is in the interests of conciseness and without limitation to the scope of the invention. Furthermore, the term 'disorders' is used further herein as an abbreviation for 'disorders and diseases'. Thus, wherever the said term is used herein, reference is intended either to 'disorders' or 'diseases' or both. The broadest meaning relevant to the context may be taken.

It is observed that in all the above disorders and other disorders of the brain and the CNS the neurodegeneration is associated with neuro muscular-degeneration. The term 'neurodegenerative' as used hereinbelow is therefore intended to refer to both and may be considered to be an abbreviation for the phrase: neurodegenerative and neuro muscular-degenerative. This is again in the interests of conciseness and the broadest meaning applicable to the context may be taken. The abovementioned disorders are referred to hereinbelow by their abbreviated names given above at the end of their names. Each of the abovementioned disorders in particular, and said neurodegenerative orders in general are actually a group of disorders having common causes or set of symptoms or both. The composition and method of the invention are applicable to each member of such groups. Other abbreviations used herein are indicated in brackets following the unabbreviated name/word.

ALS is a neurodegenerative disease and is also referred to as the Motor Neuron Disease (CMD) and as Lou Gehrlig's disease. Loss of motor neurons (MNs) in the motor cortex, brain stem and the spinal cord occurs in this disorder leading to progressive dysfunction of the Central Nervous System (CNS). ALS is attributed to gene mutations, in particular, mutation of Cu.Zn superoxide dismutase (SODI). The involvement of oxidative stress in the pathogenesis of ALS has been reported. Oxidative damage occurs in the DNA, proteins, and lipids within affected areas of the central nervous system (CNS). Apart from the direct damage caused by free radicals, oxidative stress can also disrupt other mechanisms contributing to the neurodegeneration in ALS. Thus, oxidative stress appears to cause both direct and indirect damage in neurodegeneration. It is therefore an important therapeutic target and is the subject of this invention. Both familial ALS (FALS) and sporadic ALS (SALS) are found.

Parkinson's disease (PD) is another major neurological disorder that generally affects people in old age over about 65 years. The term Parkinsonism is used for symptoms of tremor, stiffness and slowing of movement. It is caused by reduced levels of dopamine. It is a slow, progressive disease that is caused by the loss of dopamine producing neurons and other factors. Irrespective whether oxidative stress is a primary or secondary cause in PD, it has been established that oxidative damage is a significant factor in the progress of this disease. Effective delivery of suitable anti-oxidants is therefore an important consideration in the prevention, elimination, treatment and management of this disorder.

Alzheimer's disease (AD) is another age-related disease characterised by impairment of memory and dislocation in reasoning, language and perception. It has the potential to cause severe disruption in the normal life of subjects, both at work and socially. It is reported that Alzheimer's disease results from an increase in the production or accumulation of a specific protein (beta-amyloid protein) in the brain that leads to the disruption of neuronal cell functioning and signalling and ending with neuronal cell death. Other risk factors for Alzheimer's disease include hypertension, coronary heart disease, diabetes and elevated blood cholesterol. Although oxidative stress is not mentioned as a causative factor, it is reported that it is a contributory factor and antioxidative treatments provide a certain amount relief and reversal of the progress of the disease.

Multiple sclerosis (MS) is an inflammatory disease wherein the myelin sheaths around the axons of the brain and the spinal cord system suffer damage. It is also a progressive disease that can start with muscular weakness at the extremities, vision difficulties, problems with co-ordination and balance and can lead to severe cognitive disability and almost total paralysis. The causes may be auto-immune in nature or the disorder may be viral. In this disorder too, these inventors observe that oxidative stress and anti-oxidation treatment are relevant, perhaps not in the cure but in the control and management thereof.

Muscular dystrophy (MD) is characterised by the inability of the body to make the proteins required for maintaining the health of muscles. It is a genetic order that leads to the death of the muscle cells and tissue and its effect is not confined to the skeletal muscles. It mainly affects infants and children but one form of the disease strikes in later years. These inventors believe that oxidative stress is a contributory factor in the unfolding and development of this disorder and hence anti-oxidation treatment has relevance in the prevention, treatment and management thereof.

As is known oxidative stress arises from the presence of reactive oxygen species (ROS) in the cells and tissues. Another species that causes cell and tissue damage is nitrogen oxide (NO). Both are either causative factors or contributory factors or both in said neurodegenerative disorders. Both ROS and NO cause protein aggregation and lipid peroxidation. The said protein and lipid degradation is more pronounced when increased levels of glutamate, chloride and calcium are present. These processes and the physiological imbalances caused thereby finally lead to cell death.

A factor in the neuro muscular degenerative process is metabolic and muscular acidosis. The effects of acidosis are: Ca resorption from bones leading to weakening of skeletal system; failure of ATP+Ca coupling leading muscular fatigue; disintegration of the mucosal membranes therein; and failure of tissue signal transduction. The process can end in impairment of muscular co-ordination. At this stage, the autoimmune system may inflict further damage to the muscle tissue.

A number of these factors are manifestations of, or arise from oxidative stress and call for antioxidation treatment. The drawbacks in the prior art approaches to the problem of oxidative stress in said neurodegeneration is how to achieve the required serum levels of the antioxidants (particularly ascorbic acid) and to ensure that they reach the target region in the brain and the CNS in adequate concentrations.

Studies on the efficacy of Vitamin C (Ascorbic acid) in said neurodegenerative disorders have been carried but they have been inconclusive because of the problem of achieving said high serum levels and reaching the said target region. Said serum levels tend to level off in response to physiological balance mechanisms.

These inventors considered that one needs to look for a component that is a suitable carrier for the ascorbic acid across the brain barrier. Preferably the component must be able to modify said physiological control mechanism such as to enhance serum levels of ascorbic acid. The carrier should be able to build up high concentrations of ascorbic acid in the target regions in the brain. Preferably the said second component must either supplement the therapeutic activity of the ascorbic acid or possess alternative therapeutic efficacy in the context of cell and tissue damage in neurodegeneration. Said alternative efficacy may be by a different mechanism.

Apart from tackling the consequences of oxidative stress in the said disorders, the experiments by these inventors establish that administration of ascorbic acid is relevant to other disorders/diseases such as stroke, trauma, and seizures. Said experiments have also revealed the following other benefits of the therapy of the invention
  i. protection against peroxidation of unsaturated fatty acids;
  ii. increase in the collagen and glutathione synthesis;
  iii. increase in the synthesis of dopamine in the dopamine-generating neural cells (SK—N—SH cells) in subjects affected AS or PS;
  iv. countering excitotoxicity caused by calcium, chloride, glutamate and ROS by synthesising glutathione which neutralises the excitotoxicity;
  v. restoring the anti-oxidative capacity of vitamin E; and
  vi. assisting recovery in cases of haemorrhage, neurogenic atrophy of the muscles and demyelination of the nerves.

Said increase in dopamine generation occurs by two mechanisms: one at the metabolic level after short-term incubation and by increasing the tyrosine hydroxylase gene expression after long-term incubation.

Prior art appears to have assumed that higher dosages of ascorbic acid above about 1000 mg/day are not meaningful because the physiological controls in the body metabolise excess ascorbic acid. Because of that or for other reasons, prior art has also generally concluded that said higher doses have no therapeutic value in relation to the neurological and other disorders mentioned hereinabove. Prior art has also further assumed that said higher dosages are harmful in so far as they encourage formation of kidney stones or pro-oxidative toxicity.

These inventors observe that higher dosages are indeed vital for the abovementioned disorders and are the key to their cure and management. It is furthermore necessary to continuously administer said higher doses over a considerable period of time to ensure adequate uptake by the neurons. The risk of kidney stones, if any can be countered by suitable additives such as for example zinc citrate.

It is therefore the object of this invention to provide a said carrier component that can be administered together with ascorbic acid to enhance said serum levels of the latter and to facilitate and enhance the delivery thereof to the said target regions in the brain and the CNS.

It is a further object of the invention to devise dosages of ascorbic acid and said second component such that higher serum ascorbic acid levels and higher uptake by the brain neurons can be achieved.

It is a still further object of the invention to provide said additional components to reduce/minimise the risk of kidney stones.

The critical consideration therefore is to locate such a said carrier component that facilitates said access to brain and CNS tissue. It must also stabilise serum ascorbic acid at higher levels in the subjects than is achievable by the administration of ascorbic acid by itself. It must be non-toxic, non-reactive with ascorbic acid and has a good solubility in a physiologically compatible solvent that has a good solubility for ascorbic acid. Preferably the said solvent should be water or aqueous solutions for the purposes of intravenous application. The composition must be administrable to human and animal subjects intravenously, intramuscularly, transdermally and by other routes.

These inventors tried out a number of compounds and substances with these considerations in mind. It was fortuitously discovered that Mannitol is a compound that meets said requirements to a very high degree. Several other compounds were tried and were also found to be suitable but did not meet the requirements to the extent to which mannitol did which was to rapidly build up the ascorbic acid concentration in the affected brain cells. The trials were conducted on aquatic species which like humans did not internally synthesise ascorbic acid. This surprising discovery that mannitol facilitates the transport and delivery of ascorbic acid to the target tissue in adequate amounts apart from performing a supplementary and complementary therapeutic role in neurodegeneration is a very important synergy that although not directed specifically towards therapeutical efficacy is important nevertheless. It is observed by these inventors that said facilitative role is an important and useful synergy and renders the composition a synergistic composition. In addition, these inventors observe that a certain amount efficacious synergy is also present in so far as the curative effect of the composition of the invention and the disease reversal obtained is more pronounced than the sum of the effects possible with the application of mannitol and ascorbic singly.

These inventors have found that mannitol helps in reducing protein aggregation; reduces free radical formation; improves oxygen supply to the brain and regulates the body fluid levels in addition to the said facilitative role thereof in the transport and delivery of ascorbic acid.

According to the invention, therefore, there is provided a synergistic therapeutic composition for prevention, elimination, treatment and management of neurodegenerative and neuro muscular degenerative disorders and diseases in human and animal subjects, such as Amytrophic lateral sclerosis (ALS), Multiple sclerosis (MS), Alzheimer's disease (AD), Parkinson's disease (PD), and Muscular dystrophy (MD) and other, comprising a first component and a second component, said first component being mannitol in any of the forms thereof, or any of the mixtures of said forms, and said second component being ascorbic acid in any of the forms thereof such as the oxidised form, the reduced form, the mineral ascorbates, the fatty acid esters of ascorbic acid and others, or any of the mixtures of said forms.

According to the invention, therefore, there is further provided a method of treatment for prevention, elimination, treatment and management of neurodegenerative and neuro muscular degenerative disorders such as amytrophic lateral sclerosis (ALS), multiple sclerosis (MS), alzheimer's disease (AD), parkinson's disease (PD), and muscular dystrophy (MD) and others in human and animal subjects comprising the administration of a suitable dose of a composition over a pre-determined period of time and optionally followed by a maintenance dose thereof over a pre-determined period of time, said composition comprising a first component and a second component, said first component being mannitol in any of the forms thereof, or any of the mixtures of said forms, and said second component being ascorbic acid or any of the forms/derivatives thereof such as the oxidised form, the reduced form, the mineral ascorbates, the fatty acid esters of ascorbic acid and others, or any of the mixtures of said forms.

According to the invention, therefore, there is further provided a process for making a composition comprising a first component and a second component, said components being mannitol and ascorbic acid respectively, comprising providing said first component, mannitol in any of the forms thereof, or as any of the mixtures of said forms, and the said second component, ascorbic acid in any of the forms thereof such as the oxidised or the reduced form, the mineral ascorbates and the fatty acid esters of ascorbic acid or others, or any of the mixtures of said forms, followed by admixing of the former and the latter to yield said composition.

According to the invention, therefore, there is further provided a method of treatment for prevention, elimination, treatment and management of neurodegenerative and neuro muscular degenerative disorders such as amytrophic lateral sclerosis (ALS), multiple sclerosis (MS), alzheimer's disease (AD), parkinson's disease (PD), and muscular dystrophy (MD) and others in human and animal subjects comprising the administration of high ascorbic acid doses over a pre-determined period of time and optionally followed by a maintenance dose thereof over a pre-determined period of time, said dose being from one gram per day and above and comprising either ascorbic acid or any of the forms/derivatives thereof such as the oxidised and reduced forms or the mineral ascorbates or the fatty acid esters thereof or any of the mixtures thereof.

As mentioned, the composition of the invention essentially comprises mannitol and ascorbic acid. Within the scope of the invention the mannitol may be in any of the forms thereof such as D-mannitol or others or in any known converted, but pharmaceutically acceptable form. The ascorbic acid may be in the form of Vitamin C or DHA, the oxidised form of ascorbic acid, as an ascorbate and others or in a converted pharmaceutically acceptable form. The preferred forms of the two constituents are D-mannitol and ascorbic acid.

Preferably the composition of the invention further comprises zinc citrate. Zinc citrate leads to increased generation of the superoxide dismutase (SOD) and neuropathy target esterase (NTE) and other enzymes and increases energy levels.

Preferably, the composition of the invention is in the IV form suitable for intravenous administration. The IV fluid preferably comprises a Potassium phosphate buffer which helps maintain the blood pH preferably at a level of 7.4 pH.

In the preferred IV embodiment comprising the additional components, namely, zinc citrate and potassium phosphate buffer 7.4 pH, the composition of the invention ensures better homeostatis and minimises respiratory and metabolic acidosis in neurodegenerative and neuro muscular degenerative subjects.

Within the scope of the invention, the composition of the invention may be in any pharmaceutical form suitable for administration orally, intravenously, intramuscularly, by transdermal patch, nasally or by any of the other known routes. Preferably, the said composition is in IV (intravenous), IM (intramuscular), subcutaneous or patch form and more preferably in the IV form. The preferred forms are advantageous from the point of view of several objectives, in particular it avoids the physiological control that comes into action when ascorbic acid is administered orally. With oral administration the serum levels achieved are low as body metabolises the excess ascorbic acid and maintains it at a low serum level. For adequate and efficient scavenging action against the free radicals, it is essential to have high levels of ascorbic acid in the serum and at the target cells. Similarly, the composition of the invention may be in any of the known forms such as tablets, capsules, gels, solution, patch and others and may comprise any one or more of additional factors such as for further supplementary or complementary therapeutic action, for additional nutrition, for colour, texture, odour, taste and flavour and for other desirable properties.

Administration of the composition of the invention modifies the physiological control action such as to permit a higher serum level of ascorbic acid. It provides better transport and delivery of ascorbic acid component at the target cell region in the brain and the CNS by better access across the brain-blood barrier. This results in better scavenging and neutralisation of the free radicals and preventing cell death.

All proportions of the three components, namely, mannitol, ascorbic acid and zinc citrate exhibit therapeutic efficacy. Preferably, the ratio of mannitol to ascorbic acid in the composition of the invention is from about 5:1 to about 80:1 by weight. Preferably, the ratio of zinc citrate to mannitol is from about 0.007:1 to about 0.014:1 by weight. The composition of the preferred IV fluid embodiment of the invention is:

| | |
|---|---|
| Mannitol | from about 1.8% to about 25% w/v |
| Ascorbic acid | from about 0.2% to about 5.0% w/v |
| Zinc citrate | from about 0.01% to about 0.1% w/v |
| Plus Potassium phosphate Buffer | 7.4 pH |

The composition of the invention may be made by the process of admixture of the components thereof. The invention provides for high doses of ascorbic acid such as one gram thereof per day and more. In order to provide a clearer understanding of the invention and without limitation to the scope of the invention a few embodiments/examples thereof are described hereinbelow.

EMBODIMENT-1

An IV Composition
Basis: 1 liter of the intravenous solution
Mannitol 1.8%-25% w/v.
Zinc Citrate 0.01%-0.2% w/v.
Ascorbic acid 0.2-5.0% w/v.
Potassium phosphate Buffer—7.4 pH
Water—qs
Preservative—qs
Note: Monitoring of serum electrolytes initially for 30 minutes is required after administration. Urine electrolytes can also be checked.

EMBODIMENT-2

An IM Composition
Basis: 10 ml of the solution

Mannitol 500-1,000 mg
Zinc Citrate 10-100 mg
Ascorbic acid 250-2,000 mg
Water qs
Benzyl Alcohol—preservative
Sodium Hydroxide and HCl for pH adjustment.

EMBODIMENT-3

Composition for a transdermal patch
Mannitol 500-1,000 mg
Zinc Citrate 15-75 mg
Ascorbic acid 500-2,000 mg
Absorbent Gel qs
Preservative qs

EMBODIMENT-4

Basis: 30 ml of the spray solution
Composition for a Nasal Spray
Mannitol 100-500 mg
Zinc Citrate 2-15 mg
Dehydroascorbic acid 200-500 mg
Other ingredients: citric acid, sodium citrate, glycerin and benzalkonium chloride, purified water.
Olfactory neurons has direct uptake mechanism through its olfactory receptors/olfactory bulb, whereby required dehydroascorbic acid can reach brain neurons in no time and have more therapeutic effect at very smaller doses.

EMBODIMENT-5

Composition for an oral syrup 30 ml
Mannitol 5-15 g
Zinc Citrate 120-500 mg
Ascorbic Acid 5-12 gr
Other ingredients: BHT, ethyl alcohol, water, colouring agent, flavoring agent, pH adjusters.
Embodiments and variations other than described hereinabove are feasible by persons skilled in the art and the same are within the scope and spirit of this invention.

REFERENCES

1. The Influence of Mannitol on Myoglobinuric Acute Renal Failure: Functional, Biochemical, and Morphological Assessments1Richard A. Zager, 2 Charles Foerder, and Charles Bredl (J. Am. Soc. Nephrol. 1991; 2:848-855).
2. The Early Response of Mannitol Infusion in Traumatic Brain Injury Kao-Chang Lin1, Chih-Ho Chou1, Wei-Lung Chang1, Der-Shin Kel and Jinn-Rung Kuo2 (Acta Neurol Taiwan 2008; 17:26-32) (Acta Neurologica Taiwanica Vol 17 No 1 March 2008).
3. Mannitol, Furosemide, and Dopamine Infusion in Postoperative Renal Failure Complicating Cardiac Surgery Srikrishna Sirivella, MD, Isaac Gielchinsky, MD, and Victor Parsonnet, MD Department of Cardiovascular and Thoracic Surgery, Newark Beth Israel Medical Center, Newark, N.J. (SIRIVELLA ET AL Ann Thorac Surg MANNITOL INFUSION IN ACUTE RENAL FAILURE 2000; 69:501-6).
4. Effect of Mannitol on serum and Urine Electrolyte in Neurosurgical patients. Jong Hoon Kim, M.D., Kabsu Kim, M.D., and Yong Tack Nam, M.D. and Kwang Won Park, M.D. Department of Anesthesiology, Yonsei University College of Medicie, seoul, Korea. The Journal of the Korean society of Anesthesiologists: V1.25, No. 3, 1992
5. Zinc Deficiency in the Rat: Effect on serum and intestinal alkaline phosphatase activities1'2 RICHARD W. LUECKE, MARY E. OLMAN ANDBETTY V. BALTZER Department of Biochemistry, Michigan State University, East Lansing, Mich. (J. NUTRITION, 94: '68.)
6. Lowry, O. H., N. R. Roberts, M-L. Wu, W. H. Hixon and E. J. Crawford 1954 The quantitative histochemistry of brain. II. Enzyme measurements. J. Biol. Chem., 207: 7. Zinc Deficiency Exacerbates loss in Blood-Brain Barrier Integrity Induced by Hyperoxia Measured by Dynamic MRI (4477). Michael D. Noseworthy and Tammy M. Bray. Department of Human Biology and Nutritional Sciences, University of Guelph, Guelph, Ontario, Canada NIG 2W1; and Department of Human Nutrition, The Ohio state university, Columbus, Ohio 43210-1295. (P.S.E.B.M. 2000, vol 223).
8. Effect of Zinc on Lipid Peroxidation and Metal content in some Tissues of Rats. MILOS CHVAPIL, YEIMEI PENG ARTHUR L. ARONSON and CHARLES ZUKOSKI. Division of surgical Biology, Department of surgery, University of Arizona, College of Medicine, Tucson, Ariz. 85724. Jn. nutrition.org by on Aug. 7, 2009.
9. Effect of Dietary Zinc on Endogenous Free Radical production in rat Lung Microsomes. TAMMY M. BRAY, STAN KUBOW and WILLIAM .BETTGER.Department of Nutrition, college of Biological Science, University of Guelph, Ontario, Canada N1G 2W1. Jn. nutrition.org Aug. 7, 2009
10. Antioxidant-Like Properties of Zinc in Activated Endothelial Cells. Bernhard Hennig, PhD, FACN, Purushothaman Meerarani, PhD, Michel Toborek, MD, PhD, FACN and Craig J. McClain, MD, FACN Departments of Nutrition and Food Science (B.H., P.M.), Neurosurgery (M.T.), and Medicine (C.J.M.), University of Kentucky, Lexington, Ky.
11. Copper- and Zinc-containing Super oxide Dismutase Can Act as a Superoxide Reductase and a Superoxide Oxidase*. Stefan I. Liochev and Irwin Fridovich. From the Department of Biochemistry, Duke University Medical Center, Durham, N.C. 27710. THE JOURNAL OF BIOLOGICAL CHEMISTRY Vol. 275, No. 49, Issue of December 8, pp. 38482-38485, 2000
12. Essential role of Ascorbic acid Neural differentiation and Development: High levels of ascorbic acid 2-glucoside effectively enhance nerve growth factor-induced neurite formation and elongation in PC12 cells (journal of health science: 54(1) 43-49 (2008).)
13. Efficacy of Dietary Antioxidants to Prevent Oxidative Damage and Inhibit Chronic Disease1,2 Balz Frei, Linus Pauling Institute, Oregon State University, Corvallis Oreg. 97331-6512 (J. Nutr. 134:3196S-3198S, November 2004).
14. Free Radicals and Oxidative Stress in Neurodegenerative Diseases: Relevance of Dietary Antioxidants. Ravindra Pratap Singh, Shashwat Sharad, Suman Kapur (JIACM 2004; 5(3): 218-25).
15. Myenteric neurons and intestinal mucosa of diabetic rats after ascorbic acid supplementation. Priscila de Freitas, Maria Raquel Marçal Natali, Renata Va. Fernandes Pereira, Marcilio Hubner Miranda Neto, Jacqueline Nelisis Zanoni. (World J Gastroenterol 2008 Nov. 14; 14(42): 6518-6524, World Journal of Gastroenterology ISSN 1007-9327, ©2008 The WJG Press. All rights reserved.).
16. OXIDATIVE STRESS IN PARKINSON'S DISEASE Shashikant Nikam, Padmaja Nikam, S K Ahaley and Ajit V Sontakke Department of Biochemistry, Government Medical College, Miraj and KIMS, Karad Maharashtra, India (Indian Journal of Clinical Biochemistry, 2009/24 (1) 98-101).

17. Kontush A, Mann U, Arlt S, Ujeyl A, Luhrs C, Muller-Thomsen T, Beisiegel U. Influence of vitamin E and C supplementation on lipoprotein oxidation in patients with Alzheimer's disease. (Free Radic Biol Med. 2001; 31:345-354.).

18. Hitomi Takanaga et al., Sodium-dependent ascorbic acid transporter family SLC23, Pflugers Arch—Eur J Physiol (2004) 447:677-682

19. T. Caprile et Al., The Na+-dependent L-Ascorbic acid transporter SVCT2 expressed in brainstem cells, neutrons and neuroblastoma cells is inhibited by flavonoids, J. Neurochem. (2009) 108, 563-577

We claim:

1. A synergistic therapeutic composition for treatment and management of neurodegenerative and neuromuscular degenerative disorders and diseases in human and animal subjects, the composition comprising mannitol from about 1.8% w/v to about 25% w/v, zinc citrate from about 0.01% w/v to about 0.2% w/v and ascorbic acid from about 0.1% w/v to about 5% w/v, water qs, preservative qs, potassium phosphate buffer 7.4 pH, in about 100 ml of the said fluid and pro rata for other volumes; wherein the composition is in the form of an intravenous (IV) fluid.

2. The synergistic therapeutic composition as claimed in claim 1, further comprising one or more compound to provide complementary and/or supplementary therapeutic action, the one or more compound selected from the group consisting of therapeutic compounds and adjuvants.

3. The synergistic therapeutic composition as claimed in claim 1 wherein the ratio of mannitol to ascorbic acid is from about 5:1 to about 80:1 by weight.

4. The synergistic therapeutic composition as claimed in claim 1, wherein the neurodegenerative and neuromuscular degenerative disorders and diseases in human and animal subjects is selected from the group consisting of Amytrophic lateral sclerosis (ALS), Multiple sclerosis (MS), Alzheimer's disease (AD), Parkinson's disease (PD), and Muscular dystrophy (MD).

5. A synergistic therapeutic composition for treatment and management of neurodegenerative and neuromuscular degenerative disorders and diseases in human and animal subjects, the composition comprising mannitol from about 500 mg to about 1,000 mg, ascorbic acid from about 250 mg to about 2,000 mg, zinc citrate from about 10 mg to about 100 mg, water qs, benzyl alcohol preservative and sodium hydroxide and hydrochloric acid for pH adjustment in about 10 ml of the solution and pro rata for other volumes; wherein the composition is in the form of a solution suitable for intramuscular administration.

6. The synergistic therapeutic composition as claimed in claim 5, wherein the neurodegenerative and neuromuscular degenerative disorders and diseases in human and animal subjects is selected from the group consisting of Amytrophic lateral sclerosis (ALS), Multiple sclerosis (MS), Alzheimer's disease (AD), Parkinson's disease (PD), and Muscular dystrophy (MD).

7. The synergistic therapeutic composition as claimed in claim 5, further comprising one or more compound to provide complementary and/or supplementary therapeutic action, the one or more compound selected from the group consisting of therapeutic compounds and adjuvants.

8. The synergistic therapeutic composition as claimed in claim 5, wherein the ratio of mannitol to ascorbic acid is from about 5:1 to about 80:1 by weight.

9. A method for treatment and management of neurodegenerative and neuromuscular degenerative disorders, the method comprising administering a suitable dose of the composition of claim 1 to a human or an animal subject in need thereof over a pre-determined period of time and optionally followed by a maintenance dose thereof over a pre-determined period of time.

10. The method claimed in claim 9, wherein the neurodegenerative and neuromuscular degenerative disorders and diseases in human and animal subjects is selected from the group consisting of Amytrophic lateral sclerosis (ALS), Multiple sclerosis (MS), Alzheimer's disease (AD), Parkinson's disease (PD), and Muscular dystrophy (MD).

11. The method as claimed in claim 9, wherein the dose is administered intravenously.

12. A method for treatment and management of neurodegenerative and neuromuscular degenerative disorders, the method comprising administering a dose of the composition of claim 1 to a human or an animal subject in need thereof over a pre-determined period of time and optionally followed by a maintenance dose thereof over a pre-determined period of time, said dose being from one gram per day and above.

13. The method as claimed in claim 12, wherein the dose is administered intravenously.

14. The method claimed in claim 12, wherein the neurodegenerative and neuromuscular degenerative disorders and diseases in human and animal subjects is selected from the group consisting of Amytrophic lateral sclerosis (ALS), Multiple sclerosis (MS), Alzheimer's disease (AD), Parkinson's disease (PD), and Muscular dystrophy (MD).

* * * * *